United States Patent [19]
Richmond

[11] Patent Number: 4,946,448
[45] Date of Patent: Aug. 7, 1990

[54] CHECK VALVE FOR USE WITH INTRAVENOUS PUMP

[75] Inventor: Douglas S. Richmond, Mission Viejo, Calif.

[73] Assignee: Kendall McGaw Laboratories, Inc., Irvine, Calif.

[21] Appl. No.: 425,792

[22] Filed: Oct. 23, 1989

[51] Int. Cl.$^5$ .............................................. A61M 5/00
[52] U.S. Cl. ..................... 604/247; 604/81; 137/493.9; 137/512.4; 137/843
[58] Field of Search ................... 604/9, 30, 31, 80, 81, 604/118, 122, 123, 127, 246, 247; 137/493.9, 512.4, 843

[56] References Cited

U.S. PATENT DOCUMENTS

| | | | |
|---|---|---|---|
| 2,538,662 | 1/1951 | Abbott | 128/214 |
| 3,111,125 | 11/1963 | Schulte | 128/350 |
| 3,886,937 | 6/1975 | Bobo et al. | 128/214 |
| 3,888,249 | 6/1975 | Spencer | 128/214 |
| 3,924,635 | 12/1975 | Hakim | 128/350 |
| 3,976,402 | 8/1976 | Lundquist | 417/566 |
| 3,978,857 | 9/1976 | McPhee | 128/214 |
| 4,005,710 | 2/1977 | Zeddies et al. | 128/214 |
| 4,034,754 | 7/1977 | Virag | 128/214 |
| 4,141,379 | 2/1979 | Manske | 137/496 |
| 4,354,492 | 10/1982 | McPhee | 128/214 |
| 4,502,502 | 3/1985 | Krug | 137/512.3 |
| 4,556,086 | 12/1985 | Raines | 137/852 |
| 4,671,786 | 6/1987 | Krug | 604/4 |
| 4,846,836 | 7/1989 | Reich | 137/493.9 |

FOREIGN PATENT DOCUMENTS

| | | | |
|---|---|---|---|
| 0020961 | 2/1980 | Japan | 137/493.9 |
| 2094443 | 9/1982 | United Kingdom | 137/843 |

Primary Examiner—John D. Yasko
Assistant Examiner—Anthony M. Gutowski
Attorney, Agent, or Firm—Christie, Parker & Hale

[57] ABSTRACT

A medical liquid administration set is provided with a check valve which is configured to relieve excess pressure downstream from the check valve. The check valve includes a resilient valve disc and a valve seat, which engages the disc when the valve is closed. The administration set includes primary and secondary liquid sources connected through a Y-connector to a pump, which pumps liquids sequentially from the first and second sources to a patient. The check valve is disposed in the set between the Y-connector and the primary liquid source and is in its closed position with the valve disc on the valve seat when the liquid level in the secondary liquid source is higher than the liquid level in the primary source to thereby prevent backflow of liquid from the secondary source into the primary. The check valve is in its open position, allowing flow from the primary source to the patient when the liquid level in the secondary source has fallen to the level of liquid in the primary source. The valve disc is of a resilient material, and a slit is through the disc so that when the downstream pressure is greater than the upstream pressure by a selected value, the slit is forced open to relieve the excessive pressure.

18 Claims, 2 Drawing Sheets

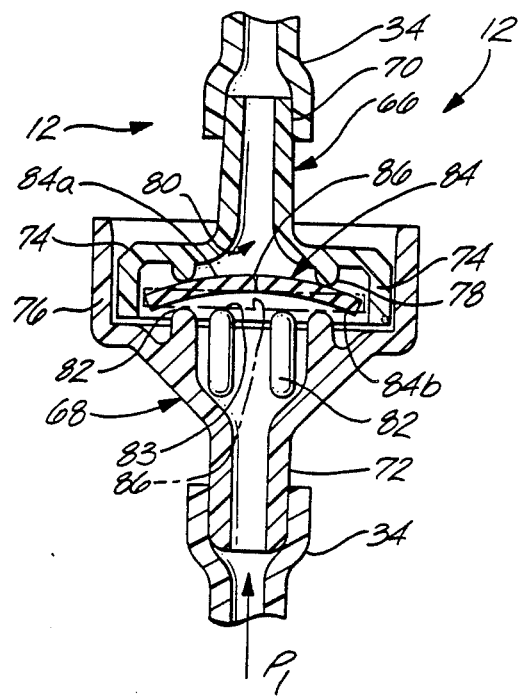
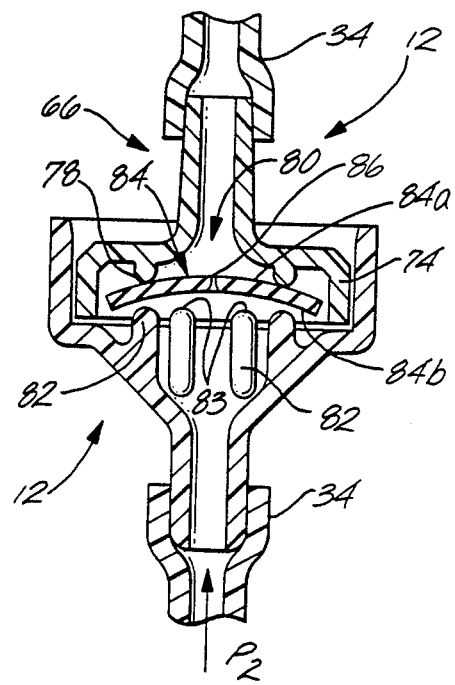

CHECK VALVE FOR USE WITH INTRAVENOUS PUMP

FIELD OF THE INVENTION

This invention relates to a medical liquid administration set incorporating a backflow check valve designed to relieve pressure downstream from the valve when the downstream pressure exceeds the upstream pressure by a selected value.

BACKGROUND OF THE INVENTION

It is often desirable to administer two medical liquids to a patient in sequence. This sequential administration can be accomplished by providing a medical liquid administration set which includes two liquid sources (a primary source and a secondary source) connected through a Y-connector from which a single tube leads through an injection needle to the patient. A tube leading from the primary source or set to the Y-connector incorporates a check valve for stopping the flow of liquids from the primary source (and for preventing backflow of liquids from the secondary source to the primary source) when the pressure at the valve from the secondary source is greater than the pressure at the valve from the primary source. A medical administration set useful for sequential administration of liquids is described in U.S. Pat. No. 4,354,492, which issued on Oct. 19, 1982 to McPhee. U.S. Pat. No. 4,354,492 is incorporated herein by this reference.

In the type of medical administration sets described in the above-referenced patent, the secondary source or set is normally positioned at a higher elevation than the primary set. When in this configuration, liquid flows from the secondary set to the patient until the liquid level in the secondary set falls to the level of the liquid in the primary set. At this time, the check valve in the tube leading from the primary set to the Y-connector opens, thereby allowing liquid to flow from the primary set to the patient.

The provision for automatic commencement of flow from the primary set to the patient ensures that there will be no interruption in the flow of liquids to the patient. This is important because such an interruption can, for example, result in blood-clotting in the injection needle, requiring needle replacement and attendant patient discomfort.

When a fine control of the amounts of the liquids being administered to the patient is desired, a positive displacement infusion pump, such as one of the pumps provided by Kendall McGaw Laboratories, Inc. of Irvine, Calif., under the trademarks "521 INTELLIGENT PUMP" or "522 INTELLIGENT PUMP," can be incorporated into the administration system. When such a pump is used, it is connected in the system in the line between the Y-connector and the patient. The check valve in the line between the primary set and the Y-connector serves to provide for automatic sequencing of liquid delivery from the pump. For example, as was the case for the above-described gravity system, when the liquid level in the secondary set falls to the level of the liquid in the primary set as it is being pumped to the patient, the check valve opens, and liquid automatically begins to be pumped from the primary set to the patient.

Pumps such as the McGaw "521" and "522" pumps include a cassette that is connected in the line between the Y-connector and the injection needle. The cassette, which is installed in the pump housing prior to operation of the system, comprises flexible chambers into which liquid flows during the pump intake stroke, and out from which liquid is forced during the pump output stroke. Prior to placing such a pump into service, the flexible cassette and the associated inlet and outlet tubing are filled with liquid from one of the liquid sources (usually the primary set) to eliminate entrapped air from the system. This process fills the entire administration set with liquid and results in excess liquid being in the cassette chambers. After the system is filled, the cassette is placed into the pumping compartment in the pump housing, and the pump housing is closed with the cassette inside. Closure of the pump housing tends to force excess liquid contained in the cassette into the lines upstream from the pump. The displaced fluid builds up pressure between the pump and the check valve, which creates an overpressure condition. The pumps are designed with an overpressure alarm and will not start unless a differential pressure of at least a selected value between the pump intake and outlet is sensed. In some instances, this can be about 75 inches of water pressure. The overpressure condition that results from closing the overfilled cassette into the pump housing is sufficient to set off the overpressure alarm and prohibit the pump from starting.

It is therefore desired that an administration set be provided which incorporates a flow-sequencing check valve that is configured to eliminate overpressure conditions which result in pump overpressure alarms and malfunctioning.

SUMMARY OF THE INVENTION

There is therefore provided in accordance with practice of this invention a medical liquid administration set which incorporates a backflow check valve in the line from the primary set that is designed to relieve pressure downstream from the check valve when the downstream pressure exceeds upstream pressure by a selected value. Such pressure relief eliminates overpressure conditions in the system and the resulting pump alarm and failure to start.

The administration set of this invention includes primary (first) and secondary (second) liquid sources and first and second conduits for connecting primary and secondary liquid sources, respectively, to a Y-connector which has its stem connected to a third conduit. Means are disposed along the path of the third conduit for pumping liquids from the primary and secondary liquid sources to the patient. A check valve, which is in the first conduit between the Y-connector and the primary liquid source, includes a housing having a valve seat and a valve member disposed therein. Means are provided in the housing for supporting the valve member downstream from the valve seat when the upstream pressure is greater than the downstream pressure. In this condition, the check valve is open, and liquid flows from the primary liquid source, through the system, to the patient.

The valve member is movable to the valve seat for preventing flow in an upstream direction through the check valve when the downstream pressure is greater than the upstream pressure by no more than a selected value. The valve member includes means for relieving downstream pressure when the downstream pressure exceeds the upstream pressure by the selected value.

BRIEF DESCRIPTION OF THE DRAWINGS

These and other features, aspects and advantages of the present invention will be more fully understood when considered with respect to the following detailed description, appended claims, and accompanying drawings, wherein:

FIG. 2 is a semi-schematic, vertical, cross-sectional view of one embodiment of the check valve of the present invention, shown in a condition where the differential between the downstream and the upstream pressures acting on the valve disc is less than the pressure at which downstream pressure is relieved; and FIG. 3 is a semi-schematic, cross-sectional view of the check valve of FIG. 2, shown in a condition where the pressure differential between the downstream and the upstream pressure on the valve disc is greater than the pressure at which the downstream pressure is relieved.

DETAILED DESCRIPTION

Figure 1:
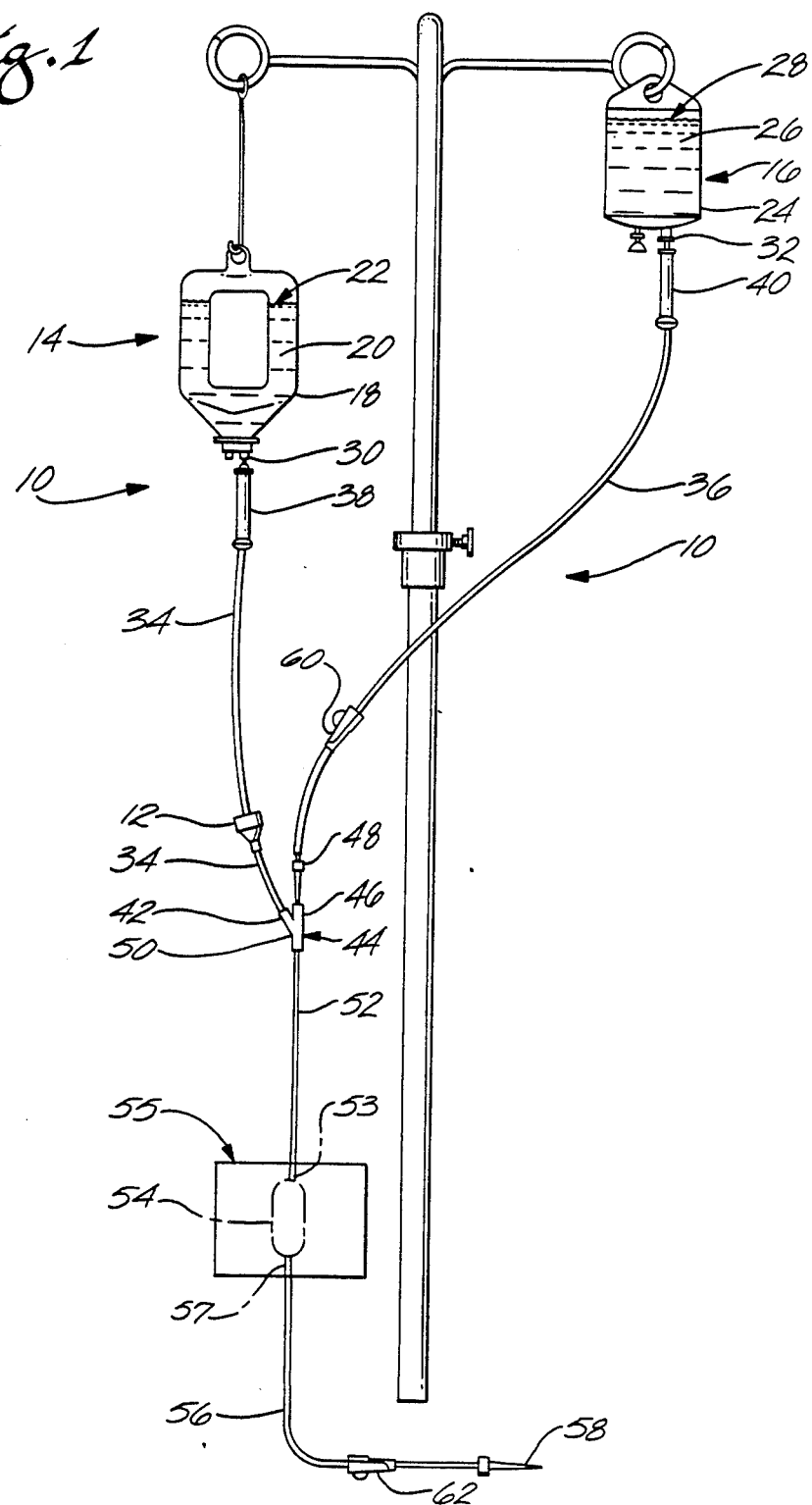
FIG. 1 is a semi-schematic view of an exemplary embodiment of an administration set including a check valve provided in accordance with practice of the present invention.

Referring to FIG. 1, there is shown a semi-schematic view of an exemplary embodiment of a medical liquid administration set 10 which incorporates a check valve 12 provided in accordance with this invention. The administration set 10 includes two liquid sources, a primary set (or source) 14 and a secondary set (or source) 16. Both the primary and secondary sets (14 and 16, respectively) are suspended in the air by means of a supporting system (unnumbered). The primary set 14 includes a container 18 containing a medical liquid 20 having a liquid level 22. The secondary set 16 includes container 24 containing a medical liquid 26 having a liquid level 28. In the illustrated embodiment, the liquid level 28 in the secondary set is at a higher elevation than the liquid level 22 in the primary set.

The containers 18 and 24 have outlets 30 and 32, respectively, connected to first and second conduits 34 and 36 via first and second drip chambers 38 and 40. The first conduit 34 is connected via the check valve 12 to a first side port 42 of a Y-connector 44, and the second conduit 36 is connected to a second side port 46 of the Y-connector. In one embodiment, the second conduit 36 is connected to the side port 46 by means of a needle 48, which punctures a diaphragm (not shown) on the port 46.

The stem 50 of the Y-connector is connected through a third conduit 52 to an inlet 53 of a flexible cassette 54 (shown in phantom in FIG. 1), which is removably housed in a pump 55, such as a "521" or a "522" diaphragm pump, described above as being sold by Kendall McGaw Laboratories, Inc. A fourth conduit 56 is connected to the outlet 57 of the flexible cassette 54, which, in turn, is connected to a needle 58, which is to be inserted into a patient to provide a pathway for intravenous adminis-tration of the medical liquids. The second conduit 36 is typically provided with a valve 60, which can be manually adjusted to shut off or regulate the flow of liquid from the secondary set. If desired, a flow control valve 62 can also be installed in the line 56 which can be opened and closed as required during the line-filling operation described below. The first, second, third, and fourth conduits are typically flexible, clear-plastic tubing, such as polyvinyl chloride.

Administration sets which incorporate backflow check valves for sequential administration of medical liquids, and the operation of such administration sets, are generally known in the art, e.g., such sets are disclosed and their operation is explained in the above-referenced U.S. Pat. No. 4,354,492. In general, to begin administration of the medical liquids (after the lines of the administration set are filled with liquid to remove entrapped air), the needle 58 is inserted into a vein of a patient while the valve 60 (if the secondary set is connected at this time) is in its closed position. If it is desired to first administer liquid from the secondary set, the valve 60 is opened and the pump 55 started. Conversely, if it is desired to first administer liquid from the primary set, the valve 60 remains closed. When the liquid level 28 of the secondary set is greater than the primary liquid level 22 and the valve 60 is open, a pressure differential on the check valve 12 will be such that it will be in its closed position, prohibiting flow from the primary set to the patient, and prohibiting backflow from the secondary set into the primary set. The check valve 12 will remain closed until the liquid level 28 falls to just below the liquid level 22 in the primary set. At this time, the valve 12 will automatically open, which allows flow of liquid from the primary set 14 to the patient.

The construction and operation of the check valve 12 provided in accordance with this invention can be understood by referring to FIGS. 2 and 3. In a preferred embodiment, the check valve 12 includes an upper housing member 66 and a lower housing member 68 connected to the first conduit 34 at upper and lower tubular adapters 70 and 72 of the housing members, respectively. The upper and lower housing members can be formed of injection-molded plastic material, such as polyvinyl chloride, polycarbonate, or the like.

The upper housing member 66 includes a cylindrical skirt portion 74, which extends downwardly from the upper tubular adapter 70 and fits telescopically into a cylindrical skirt portion 76 of the lower housing member 68, which extends upwardly from the lower housing tubular adapter 72. A valve seat 78 extends downwardly and is around an opening 80 from the upper tubular adapter 70 into the interior of the cylindrical skirt portion 74. The lower housing member 68 includes a series of projections or prongs 82, e.g., 3 to 12 such projections, which are generally cylindrical and which have rounded ends, or tips, 83 extending upwardly and facing the valve seat 78. The projections 82 are closely spaced to the valve seat 78 and are positioned roughly in opposition thereto. In one preferred embodiment, eight such projections 82 are provided. The projections support a valve disc 84 when the check valve 12 is in its open condition, permitting liquid to flow from the primary set 14 to the patient. When the disc is in the open condition (shown by dashed lines in FIG. 2), liquid flows downwardly through the line 34, through the check valve upper housing 66, between the edge of the valve disc 84 and the interior of the skirt 74, through the spaces between the projections 82, out through the lower housing, and into the downstream portion of the system. The rounded tips 83 of the projections 82 reduce the area of contact between the projections and the disc to less than 20% of the disc's bottom surface area.

As is noted above, the check valve 12 prevents flow from the primary set 14 downstream through the valve, and also prevents flow from the secondary set upstream through the valve whenever liquid level 28 in the secondary set 16 is elevated higher than the liquid level 22 in the primary set. In this situation, the pressure downstream from the disc is higher than the upstream pressure, which forces the valve disc 84 against the valve seat 78, thereby preventing flow of liquid through the check valve.

In an exemplary embodiment, the check valve disc 84 has a uniform thickness, preferably from about 0.010 inch to about 0.040 inch, and is made of a resilient material, such as natural rubber, silicone rubber, or the like. Preferably, the disc thickness is from about 0.020 inch to about 0.028 inch and is of natural rubber. The disc 84 is substantially flat in its unloaded condition, having a flat upstream-facing surface 84a, which is parallel to a flat downstream-facing surface 84b. The disc downstream-facing surface 84b rests on the rounded top ends 83 of the projections 82, as is shown in phantom in FIG. 2, when the upstream pressure is greater than the downstream pressure. As mentioned above, when in this condition, fluid flow is in the direction opposite that of the arrow $P_1$, i.e., the flow passes downwardly through the valve 12. When the liquid level 28 is higher than the level 22 and the check valve 12 closes, the disc moves against the valve seat 78 and bows, as is shown in FIG. 2. (solid lines). In accordance with practice of the present invention, the check valve is configured so that it will prevent flow from a location in the system downstream from the check valve to a location upstream from the check valve when the downstream pressure is greater than the upstream pressure by no more than a selected value. The check valve 12 includes means to automatically relieve the downstream pressure when the downstream pressure exceeds the upstream pressure by the selected value.

In a preferred embodiment, the component of the check valve 12 which provides a means for relieving excessive downstream pressure includes a slit 86, which is formed through the valve disc 84 extending from its upstream-facing surface 84a to its downstream-facing surface 84b. The disc provided in accordance with this invention can be formed, for example by die-cutting from sheet material. The disc 84 is shown in FIG. 2 in solid lines, with the slit 86 closed to prevent backflow. The slit remains closed as long as the downstream pressure, i.e., the backflow pressure $P_1$, is less than a selected value above the upstream pressure. When the downstream pressure becomes greater than the upstream pressure by the selected value, the slit opens to relieve the downstream pressure by allowing some liquid to flow in an upstream direction through the open slit. The pressure at which the slit opens to relieve downstream pressure is called the "cracking pressure." Referring particularly to FIG. 3, the disc is shown in a condition when the downstream pressure, i.e., the backflow pressure $P_2$, exceeds the cracking pressure $P_c$. In this condition, the disc bows sufficiently to cause the slit 86 to open, thereby relieving downstream pressure. When the downstream pressure returns to less than the cracking pressure, the slit closes to reseal the disc, preventing further flow. Each time the downstream pressure exceeds the cracking pressure, the pressure relief-and-resealing cycle is repeated.

The combination of the type of material from which the disc is formed, the thickness of the disc, and the size of the slit determine the cracking pressure. For example, when relatively-thick discs are provided, with the other parameters being equal, the cracking pressure will be relatively higher than when relatively-thinner discs are provided. The correct combination of disc thickness, disc material, and slit size can be readily determined to provide the desired cracking pressure.

When the pump 55 is being readied for operation in the administration set 10, the differential between the downstream pressure and the upstream pressure can increase well above the pressure differential resulting from the difference in the liquid levels 22 and 28 of the primary and secondary sets, respectively. For example, as is described above, the pump 55 includes a cassette 54, which is installed in the pump housing prior to operation of the system. The cassette includes a flexible chamber into which liquid flows during the pump intake stroke and out from which liquid is forced during the pump outlet stroke. Prior to placing the pump 55 in service, the flexible cassette 54 (and the associated inlet and outlet tubing) are filled with liquid from one of the liquid sources to eliminate entrapped air from the system. This process fills the entire administration set 10 with liquid and results in excess liquid being in the flexible cassette chamber. After the system is filled and the valve 62 is closed, the cassette 54 is placed into the pumping compartment in the pump housing, and the pump housing is closed with the cassette inside. Closure of the pump housing tends to force excess liquid contained in the cassette into the lines 52 and 34 upstream from the pump. When a standard check valve is used, i.e., one that does not incorporate the downstream pressure relief feature of check valve 12 provided in accordance with this invention, the displaced fluid builds up pressure between the pump and the check valve, setting off a pump overpressure alarm and prohibiting the pump from starting. Conversely, when the check valve 12 of the present invention is installed, and the backpressure reaches the selected cracking pressure, the slit 86 opens, as is shown in FIG. 3. This allows liquid to flow in an upstream direction through the check valve, thereby relieving the overpressure condition which prevents the pump from alarming.

In accordance with this invention, the combination of disc material, disc thickness, and disc size is selected such that the cracking pressure is of a magnitude that is not encountered when pump backpressure is normal. That is, it is preferable that the slit open only during the initial filling of the cassette 54 and its installation into the pump housing. The cracking pressure is preferably in a range of from about 40 inches to about 75 inches of water pressure, preferably about 45 inches of water pressure. The cracking pressure is preferably of a sufficiently-high value so that liquid cannot drain from the secondary set into the primary set when the secondary and primary sets are at the maximum height differential expected to be encountered during operation, i.e., about 40 inches. Thus, it is preferred that the cracking pressure be a minimum of about 40 inches of water pressure. The cracking pressure should also be of a sufficiently-low value to eliminate pump alarms and the non-start interlock feature. In this case, it is preferred that the cracking pressure be no more than about 75 inches of water pressure.

EXAMPLE 1

In one exemplary embodiment of check valves 12 provided in accordance with this invention, the discs 84 were die-cut from a sheet of natural rubber having a shore A hardness of 56 ±4. The discs had a diameter of approximately 0.35 inch and were about 0.028-inch thick, with each disc having a 0.130-inch slit through its center. One hundred twenty-three (123) of the above-described check valves were assembled and tested to determine the cracking pressure of the discs. The valves were installed, one at a time, onto the end of a line connected to a water container. In each test, the container was elevated above the height of the check valve, and the valve disc was observed for slit opening. At the point the slit opened (when the cracking pressure was reached), the height of the water above the valve was recorded. The results of the tests were as follows: The mean cracking pressure was 60.9 inches of water pressure, and the range of cracking pressure was from 49 to 73 inches of water pressure.

EXAMPLE 2

A test was conducted to determine the variations in cracking pressure of check valve discs provided in accordance with this invention as a function of slit width.

Check valves, such as those described above with reference to FIGS. 1-3, were assembled using discs made of the same material as the discs used in Example 1. Each disc was 0.019-inch thick, with one of the discs having a 0.090-inch slit through its center, and the other disc having a 0.100-inch slit. The cracking pressure of the discs was as follows:

| Slit Width (inches) | Cracking Pressure (inches water pressure) |
|---|---|
| 0.090 | 45 |
| 0.100 | 39 |

EXAMPLE 3

A test was conducted to determine the variations in cracking pressure of check valve discs provided in accordance with this invention as a function of disc thickness.

Three check valves, such as those described above with reference to FIGS. 1-3, were assembled using discs made of the same material as the discs used in Example 1. Each of the discs had a slit through its center which measured 0.130 inch in length. The thickness of the discs was 0.025, 0.030, and 0.035 inch, respectively. The cracking pressure of the discs was as follows:

| Disc Thickness (inches) | Cracking Pressure (inches water pressure) |
|---|---|
| 0.025 | 42 |
| 0.030 | 55 |
| 0.035 | 70 |

The improved check valve and administration system provided in accordance with this invention result in backflow pressure spikes being relieved to avoid pump malfunction and false alarm initiation, while preventing flow from the secondary set into the primary set.

The above description of preferred embodiments of a medical administration set 10 and its associated backflow check valve 12 provided in accordance with this invention is for illustrative purposes. Because of variations which will be apparent to those skilled in the art, the present invention is not intended to be limited to the particular embodiment described above. For example, the slit provided through the center of the disc of the check valve can have a shape other than a single line (it can be in the form of an "X" or can have other shapes).

The scope of the invention is defined in the following claims.

What is claimed is:

1. A check valve for incorporation into a liquid supply system for preventing flow from a location in the system downstream from the check valve to a location upstream from the check valve when the downstream pressure is greater than the upstream pressure by no more than a selected value, the check valve comprising:
    a housing configured to be disposed in the system between an upstream liquid source and a downstream portion of the system;
    a valve seat disposed in the housing;
    a valve member disposed in the housing having an upstream-facing surface and a downstream-facing surface; and
    means in the housing for supporting the valve member downstream from the valve seat when the upstream pressure is greater than the downstream pressure, the valve member being movable to the valve seat for preventing flow in an upstream direction through the check valve when the downstream pressure is greater than the upstream pressure by no more than a selected value, the valve member including means for relieving downstream pressure when the downstream pressure exceeds the upstream pressure by the selected value.

2. The check valve according to claim 1 wherein the valve member comprises a resilient material, and the pressure-relieving means comprises a slit through the valve member extending from its upstream-facing surface to its downstream-facing surface.

3. The check flow valve according to claim 1 wherein the valve member comprises a rubber disc having a slit through about its center extending from its upstream-facing surface to its downstream-facing surface.

4. The check flow valve according to claim 1 wherein the housing comprises:
    a lower housing member and an upper housing member, the upper housing member having a tubular adapter at its upstream end and a valve seat proximate its downstream end, the upper housing member being telescopically inserted into the lower housing member, wherein the lower housing member has a tubular adapter at its downstream end, wherein the valve member support means are proximate the upstream end of the lower housing member and comprise a plurality of projections, and wherein the valve member comprises a flexible disc, having a slit therethrough, extending from its upstream-facing surface to its downstream-facing surface, the valve member being positioned between the upper and lower housing members such that the valve member abuts the projections when the check valve is open and abuts the valve seat when the check valve is closed.

5. The valve member according to claim 1 wherein the selected pressure value is from about 40 inches to about 75 inches of water pressure.

6. The valve member according to claim 1 wherein the selected pressure value is about 45 inches of water pressure.

7. In a check valve for preventing liquid flow from downstream thereof to upstream thereof when the downstream pressure is greater than the upstream pressure by no more than a selected value, the check valve comprising a flexible valve disc, a housing comprising a lower housing member connected to an upper housing member, wherein the lower housing member includes means for supporting the valve disc when the valve is open, to thereby permit liquid flow from upstream thereof to downstream thereof and wherein the upper housing member includes a valve seat for engaging the valve disc when the valve is closed, the improvement comprising means formed in the valve disc for relieving downstream pressure when the downstream pressure exceeds the upstream pressure by the selected value.

8. The check valve according to claim 7 wherein the valve disc is formed of a resilient material, and the pressure-relieving means comprises a slit through the disc.

9. The check valve according to claim 8 wherein the valve disc is formed of rubber, and the slit is through the disc at about its center.

10. The check valve according to claim 7 wherein the lower housing member has a tubular adapter at its downstream end, the valve disc support comprises a plurality of projections connected to the lower housing member, with the ends of the projections extending toward its upstream end, wherein the upper housing member is telescopically inserted into the lower housing member and wherein the upper housing member has a tubular adapter at its upstream end and the valve seat is formed integrally with the upstream member proximate its downstream end, the valve disc comprising a flexible material having a slit therethrough and being located between the upper and lower housing members such that the valve disc abuts the plurality of projections when the valve is open, thereby permitting liquid to flow from upstream of the check valve to downstream thereof and such that the valve disc abuts the valve seat when the valve is closed.

11. The check valve according claim 7 wherein the selected pressure value is from about 40 inches to about 75 inches of water pressure.

12. The valve member according to claim 7 wherein the selected pressure value is about 45 inches of water pressure.

13. A medical liquid administration set for administering first and second liquids to a patient comprising:
 a first liquid source;
 a second liquid source;
 connector means for combining two flows into one flow;
 first conduit means for connecting the first liquid source to the connector means;
 second conduit means for connecting the second liquid source to the connector means;
 third conduit means for connecting the one flow from the connector means to the patient;
 means disposed along a path of the third conduit means for pumping liquids from the first and second liquid sources to the patient; and
 a check valve disposed along a path of the first conduit means for preventing liquid flow from downstream of the check valve to upstream thereof when the downstream pressure is greater than the upstream pressure by no more than a selected value, the check valve comprising a housing, a valve seat disposed in the housing, a valve member disposed in the housing having an upstream-facing surface and a downstream-facing surface, means in the housing for supporting the valve member downstream from the valve seat when the upstream pressure is greater than the downstream pressure, the valve member being movable to the valve seat for preventing flow in an upstream direction through the check valve when the downstream pressure is greater than the upstream pressure by no more than a selected value, the valve member including means for relieving downstream pressure when the downstream pressure exceeds the upstream pressure by the selected value.

14. The administration set according to claim 13 wherein the valve member comprises a resilient material, and the pressure-relieving means comprises a slit through the valve member extending from its upstream-facing surface to its downstream-facing surface.

15. The administration set according to claim 13 wherein the valve member comprises a rubber disc with a slit through about its center extending from its upstream-facing surface to its downstream-facing surface.

16. The administration set according to claim 13 wherein the housing comprises upper and lower housing members, the valve member support means comprising a plurality of projections connected to the lower housing member, the valve seat being formed integrally with the upper housing member proximate its downstream end, wherein the lower housing member has a tubular adapter at its downstream end and the upper housing member has a tubular adapter at its upstream end, the upper housing member being telescopically inserted into the lower housing member, wherein the valve member comprises a flexible sheet having a slit therethrough and is situated between the upper and lower housing members such that the valve member abuts the projections when the valve is open and abuts the valve seat when the valve is closed.

17. The administration set according to claim 13 wherein the selected pressure value is about 40 inches to about 75 inches of water pressure.

18. The administration set according to claim 13 wherein the selected pressure value is about 45 inches of water pressure.

* * * * *